United States Patent
O'Brien et al.

(10) Patent No.: US 8,535,712 B2
(45) Date of Patent: *Sep. 17, 2013

(54) RADIATION SENSITIVE LIPOSOMES

(75) Inventors: David F. O'Brien, Tucson, AZ (US);
Kathy A. McGovern, Tucson, AZ (US);
Bruce Bondurant, Tucson, AZ (US);
Robert Sutherland, Menlo Park, CA (US)

(73) Assignees: Varian Medical Systems, Inc., Palo Alto, CA (US); Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,058

(22) Filed: Sep. 10, 2012

(65) Prior Publication Data

US 2013/0053618 A1 Feb. 28, 2013

Related U.S. Application Data (63) Continuation of application No. 12/902,059, filed on Oct. 11, 2010, which is a continuation of application No. 11/317,833, filed on Dec. 22, 2005, now abandoned, which is a continuation of application No. 09/728,716, filed on Nov. 30, 2000, now Pat. No. 6,989,153.

(60) Provisional application No. 60/168,100, filed on Nov. 30, 1999.

(51) Int. Cl.
*A61K 9/127* (2006.01)

(52) U.S. Cl.
USPC ....... 424/450; 424/1.21; 424/9.321; 424/9.51

(58) Field of Classification Search
USPC ............................ 424/450, 1.21, 9.321, 9.51
See application file for complete search history.

(56) References Cited

U.S. PATENT DOCUMENTS

| 5,061,484 A | 10/1991 | Heidebrandt |
| 5,366,881 A | 11/1994 | Singh et al. |

(Continued)

FOREIGN PATENT DOCUMENTS

| JP | H05-502675 A | 5/1995 |
| JP | H10-506395 A | 6/1998 |
| WO | 91/09629 A1 | 7/1991 |
| WO | 96/10392 A1 | 4/1996 |

OTHER PUBLICATIONS

Lamparski, H., et al in Biochemistry, vol. 31, No. 3, pp. 685-694, 1992.*

(Continued)

*Primary Examiner* — Gollamudi Kishore
(74) *Attorney, Agent, or Firm* — Kilpatrick Townsend & Stockton LLP

(57) ABSTRACT

The present invention relates to a radiation sensitive liposome, and the use of this liposome as carrier for therapeutic and diagnostic agent(s). In particular, the invention encompasses a liposomal delivery system, comprising a stable liposome-forming lipid and a polymerizable colipid, a fraction of which polymerizable colipid polymerizes upon exposure to ionizing radiation, thereby destabilizing the liposomal membrane. Destabilization of liposomes allows for leakage of liposomal contents. The present invention further contemplates methods of diagnosing and treating conditions and diseases that are responsive to liposome-encapsulated or associated agents.

10 Claims, 5 Drawing Sheets bis-SorbPC (1)

bis-DenPC (2)    bis-AcrylPC (3)

Selected Polymerizable
Phosphatidylcholines used in Radiation
Sensitive Liposomes (56) References Cited

U.S. PATENT DOCUMENTS

| | | | |
|---|---|---|---|
| 5,650,393 A | 7/1997 | Pavia et al. | |
| 6,028,066 A * | 2/2000 | Unger | 514/180 |
| 6,159,443 A * | 12/2000 | Hallahan | 424/1.17 |
| 6,180,135 B1 | 1/2001 | Charych et al. | |
| 6,531,156 B1 | 3/2003 | Clark et al. | |
| 6,989,153 B2 | 1/2006 | O'Brien et al. | |
| 7,078,015 B2 * | 7/2006 | Unger | 424/9.52 |
| 2002/0006914 A1 * | 1/2002 | Sobol et al. | 514/44 |
| 2008/0314767 A1 | 12/2008 | Lai et al. | |
| 2009/0091325 A1 | 4/2009 | Haywood | |

OTHER PUBLICATIONS

Woodle, M.C., in Biochimica et Biophysica Acta, vol. 1113, pp. 171-199, 1992.*

Akama, Kazuhiro et al., "γ-Ray irradiation of liposomes of polymerizable phospholipids containing octadeca-2,4-dienoyl groups and characterization of the irradiated lipsomes," *J. Mater. Chem.* (2000) 10:1047-1059.

Bennett and O'Brien, "Photoactivated Enhancement of Liposome Fusion," (1995) *Biochemstry*, 34:3102-3113.

Bondurant et al., "Photoinitiated Destabilization of Sterically Stabilized Liposomes," (2001) *Biochimica et Biophysica Acta*, 1511:113-122.

Bristow, R. G. et al., "Molecular and Cellular Basis of Radiotherapy," (1998) *The Basic Science of Oncology*, 3$^{rd}$ Ed., 295-300.

Ellens, H. et al., "Membrane Fusion and Inverted Phase," (1989) *Biochemistry* 28:3692-3703.

Hosoi, F. et al., "Radiation-Induced Polymerization of Unsaturated Phospholipid Mixtures for the Synthesis of Artificial Red Cells," (1997) *Nuclear Instruments and Methods in Physics Research B* 131:329-334.

"In Situ Activation of Microencapsulated Drugs," (Sep. 2000) *Nasa Tech Briefs*, p. 64.

Kong, G. et al., "Efficacy of Liposomes and Hyperthermia in a Human Tumor Xenograft Model: Importance of Triggered Drug Release," (2000) *Cancer Res.* 60:6950-6957.

Lamparski, H. et al., "Thermotropic Properties of Model Membranes Composed of Polymerizable Lipids. 1. Phosphatidylcholines Containing Terminal Acryloyl, Methacryloyl, and Sorbyl Groups," (1993) *J. Am. Chem. Soc.* 115:8096-8102.

Matsumoto, A. et al., "Solid-State Photopolymerization of Octadecyl Sorbate to Yield an Alternating Copolymer with Oxygen," (1998) *Macromol. Chem. Phys.* 199:2511-2516.

Miller et al., "Effect of Liposomal Composition on Photoactivated Liposome Fusion," (1996) *Biochemistry* 35:11782-11790.

O'Brien and Tirrell, "Photoinduced Reorganization of Bilayer Membranes," (1993) *Bioorganic Photochemistry* 2:111-167.

Silvander, "Effects of PEG-lipids on permeability of Phosphatidylcholine/Cholesterol Liposomes in Buffer and in Human Serum," (1998) *Chemistry and Physics of Lipids* 97:15-26.

Spratt, Tony et al., "Rapid Release of Liposomal Contents upon Photoinitiated Destablization with UV Exposure," (2003) *Biochimica et Biophysica Acta* 1611:35-43.

Tsuchida, E. et al., "Polymerization of Unsaturated Phospholipids as Large Unilamellar Liposomes at Low Temperature," (1992) *Macromolecules* 25:207-212.

An Office Action from JP 2011-083861, dated Mar. 5, 2013.

* cited by examiner

Mono-substituted Radiation Sensitive Lipids

Sorbyl, Acryloyl, Methacryloyl, Vinyl ester, Dienoyl

FIGURE 3

Bis-substituted Radiation Sensitive Lipids

Sorbyl, Acryloyl, Methacryloyl, Vinyl ester, Dienoyl

FIGURE 4

Additional Radiation Sensitive Lipids

Diacetylenyl, Dienyl, Dienoyl dienyl, Dienoyl sorbyl, Dienoyl acryloyl

FIGURE 5: Selected Polymerizable Phosphatidylcholines used in Radiation Sensitive Liposomes

RADIATION SENSITIVE LIPOSOMES

BACKGROUND OF THE INVENTION a) Field of the Invention

The present invention relates to radiation sensitive liposomes and the use of these liposomes as carriers for therapeutic and diagnostic agents. The invention further relates to methods of producing the radiation sensitive liposomes and to methods of diagnosing and treating cancer and other conditions and diseases.

b) Description of Related Art

Liposomes are microscopic vesicles consisting of concentric lipid bilayers. Structurally, liposomes range in size and shape from long tubes to spheres, with dimensions from a few hundred Angstroms to fractions of a millimeter. Regardless of the overall shape, the bilayers are generally organized as closed concentric lamellae, with an aqueous layer separating each lamella from its neighbor. Vesicle size normally falls in a range of between about 20 and about 30,000 nm in diameter. The liquid film between lamellae is usually between about 3 and 10 nm. A variety of methods for preparing liposomes have been described in the literature. For specific reviews and information on liposome formulations, reference is made to reviews by Pagano and Weinstein (*Ann. Rev. Biophys. Bioeng.* 1978, 7:435-68) and Szoka and Papahadjopoulos (*Ann. Rev. Biophys. Bioeng.* 1980, 9:467-508) and additionally to U.S. Pat. Nos. 4,229,360; 4,224,179; 4,241,046; 4,078,052; and 4,235,871, the disclosures of which are incorporated by reference herein.

Biological cell membranes exploit the amphiphilic nature of lipids to create anatomical boundaries, e.g., the plasma membrane and the mitochrondrial membrane. During the early 1960s researchers demonstrated that certain classes of lipids, especially glycerophospholipids, could be used to form protein-free model membranes. They developed methods for the preparation of supported bilayer lipid membranes (BLM) and discovered that dried thin films of phospholipids spontaneously hydrate to yield self-supported closed bilayer assemblies of several thousand lipid molecules, i.e., liposomes. The lipid bilayer in each model membrane is a two-dimensional fluid composed of lipids with their hydrophilic head groups exposed to water and their hydrophobic tails aggregated to exclude water. The bilayer structure is highly ordered, yet dynamic due to the rapid lateral motion of the lipids within the plane of each half of the bilayer.

Typically, liposomes can be divided into three categories based on their overall size and the nature of the lamellar structure. The three classifications, as developed by the New York Academy Sciences Meeting, "Liposomes and Their Use in Biology and Medicine," of December, 1977, are multi-lamellar vesicles (MLV's), small uni-lamellar vesicles (SUV's) and large uni-lamellar vesicles (LUV's). SUV's range in diameter from approximately 20 to 50 nm and consist of a single lipid bilayer surrounding an aqueous compartment. Unilamellar vesicles can also be prepared in sizes from about 50 nm to 600 nm in diameter. While unilamellar vesicles are of fairly uniform size, MLV's vary greatly in size up to 10,000 nm, or thereabouts, are multi-compartmental and contain more than one bilayer. LUV liposomes are so named because of their large diameters which range from about 600 nm to 30,000 nm; they can contain more than one bilayer.

Liposomes may be prepared by a number of methods, not all of which can produce the three different types of liposomes. For example, ultrasonic dispersion by means of immersing a metal probe directly into a suspension of MLV's is a common way for preparing SUV's. Preparing liposomes of the MLV class usually involves dissolving the lipids in an appropriate organic solvent and then removing the solvent under a gas or air stream. This leaves behind a thin film of dry lipid on the surface of the container. An aqueous solution is then introduced into the container with shaking in order to free lipid material from the sides of the container. This process disperses the lipid, causing it to form into lipid aggregates or liposomes. Liposomes of the LUV variety may be made by slow hydration of a thin layer of lipid with distilled water or an aqueous solution. Alternatively, liposomes may be prepared by lyophilization. This process comprises drying a solution of lipids to a film under a stream of nitrogen. This film is then dissolved in a volatile, freezable, organic solvent, e.g., cyclohexane or t-butanol, frozen, and placed on a lyophilization apparatus to remove the solvent. To prepare a pharmaceutical formulation containing a water-soluble drug, an aqueous solution of the drug is added to the lyophilized lipids, whereupon liposomes are formed.

Lipophilic drugs may be incorporated into the bilayer by dissolving them with the lipid in the organic phase and then removing the organic phase. Hydration with the aqueous phase will result in the incorporation of the lipophilic drug into the liposomal bilayer structure. This applies both to lyophilization and thin film methods. The ratio of drug to lipid may be up to about 20% by weight, preferably from about 0.001% to about 0.1%. The encapsulation characteristics and biocompatibility of liposomes make them ideal carriers for therapeutic agents. Research efforts have been devoted to the development of liposomes for the delivery of drugs in the body. Successful in vitro studies have led to clinical trials of liposome-encapsulated amphotericin B, anthracyclines, and other drugs. Suitably designed liposomes can extend the circulation time and target the drug to particular tissues of the body (Allen, T. M., *Liposome Res.* 1992, 2:289-305; Allen, T. M., *Trends Pharm. Sci.* 1994, 15:215-220; Blume et al., *Biochim. Biophys. Acta* 1993, 1149:180-184; Klibanov et al., *J. Liposome Res.* 1992, 2:321-334; Lasic et al., *D. Science* 1995, 267:1275-1276; Lasic et al., *Stealth Liposomes*, CRC Press: Boca Raton, Fla., 1995). The delivery of liposomes to the desired sites depends in part on long circulation times in the body, which can only be accomplished by reducing the uptake of liposomes by the mononuclear phagocytic system (MPS). In recent years several means have been described to sterically stabilize liposomes in order to increase their period of circulation (Lasic et al., *Stealth Liposomes*, supra; Woodle et al., *Biochim. Biophys. Acta* 1992, 1113:171-199). A frequently used method is the attachment of poly(ethylene glycol) (PEG) to some of the lipids in the liposome. This is usually accomplished by the chemical reaction of PEG or its derivatives with the amino function of phosphatidylethanolamines (PE), e.g., methyl-PEG coupled to PE via a carbamyl linkage (Allen et al., *Biochim. Biophys. Acta* 1991, 1066:29-37); activation of methoxy-PEG with cyanuric acid (Klibanov et al., *FEBS Lett.* 1990, 268:235-243; Mori et al., *FEBS Lett.* 1991, 284:263-271); and conjugation of PEG to PE with succinimidyl succinate (Klibanov et al., *FEBS Lett.*, supra; Mori et al., *FEBS Lett.*, supra; Woodle et al. *Proceed. Intern. Symp. Control. Rel. Bioact. Mater* 1990, 17:77). PEG-modified PE may be incorporated into liposomes by including it with the other lipids during the formation of the liposomes. Alternatively, monomethoxy-PEG has been coupled to the outer surface of preformed liposomes, which contains some fraction of PE (Senior et al., *Biochim. Biophys. Acta* 1991, 1062:77-82). Regardless of the means of PEG incorporation, the inclusion of PEG ranging in size from about 1000 to 5000 daltons results in liposomes with an order of magnitude or greater increase in circulation time in the body. The useful mole fraction of PEG/PE depends on the polymer chain length. Thus 5 mole percent of $PEG_{1900}$, wherein the 1900 indicates the number average molecular weight of the PEG, was effective in achieving increased circulation time, whereas 15 mole percent of $PEG_{750}$ was necessary to achieve a comparable stabilization (Allen et al., *Biochim. Biophys. Acta*, supra). These results suggest that a minimum necessary surface coverage of the liposome is achieved at a lower mole fraction of the longer polymer. Many studies have utilized 100 nm diameter LUV composed of various phosphatidylcholines (PC) and PEG-PE or PC/cholesterol/PEG-PE in different molar ratios (Woodle et al., *Biochim. Biophys.* Acta, supra). The incorporation of PEG-PE into LUV composed of PC/PE is effective in increasing their circulation time. Although larger liposomes generally have a shorter circulation time than 100 nm LUV, it has been shown that the inclusion of PEG-PE in liposomes as large as 250 nm increases their circulation time (Woodle et al., *Biochim. Biophys. Acta*, supra). Steric stabilization of liposomes by PEG-PE is reported to be effective for liposomes in both the solid-analogous and liquid-analogous phases (Allen et al., *Liposome Res.*, supra).

In addition to extended circulation times, the successful delivery of liposomes to specific tissue sites requires the liposomes to enter the interstitium. Tumors represent a specific tissue site of considerable therapeutic interest; several research groups have reported the increased localization of sterically stabilized liposomes (PEG-liposomes) at tumor sites. The increased permeability of the vasculature at tumor sites (due to angiogenic factors secreted by tumors) allows liposomes to escape the capillaries to reach the tumor interstitial space. Sterically stabilized liposomes are more likely to accumulate at these sites because of their sustained concentration in the blood. Furthermore, it is known that the hydrophilic surface polymer may facilitate the transit from the capillaries to the tumor site. Reports of passive targeting of PEG-liposomes to tumors, including murine colon carcinomas, murine lymphomas, murine mammary carcinomas, human squamous cell lung carcinomas in SCID mice are known in the art. Specific targeting via antibodies coupled to liposomes has been observed as well. Antibody (mAb) conjugated sterically stabilized liposomes are known to localize at squamous cell carcinomas of the lung in mice and effectively deliver doxorubicin to these sites. Although the coupling of mAbs to conventional liposomes appears to increase their rate of clearance from the blood stream, the mAb conjugated PEG-liposomes, remain in circulation long enough to accumulate at their target cells.

In order for the liposomes to reach the target site without significant loss of their contents, passive leakage must be slow relative to the time required for liposomes to circulate and escape the vasculature. However, it has been shown that once sterically stabilized liposomes have accumulated at tumor sites the slow passive leakage of encapsulated chemotherapeutics, e.g., doxorubicin, can significantly affect the cells at that site. It would be desirable to stimulate enhanced release of the encapsulated agent(s) from the liposomes once the liposomes are at the target site. Ideally, such a stimulus would be spatially and temporally selective, in a manner analogous to photodynamic therapy. In photodynamic therapy, certain porphyrins and other photosensitizers are administered systemically, absorbed by cells, and upon exposure to visible light focused at the target site. Hence, the photodynamic effect results in the localized destruction of the target cells. This effect has proven useful for the treatment of cancer cells in areas of the body that are accessible to coherent light via fiber optics. In principle, the successful use of light (or other forms of radiation) to treat disease can be broadened to include a wide variety of therapeutic agents, particularly, if light is used to release the agent.

Several strategies have been employed to design photosensitive liposomes. These include the photochemical modification of individual lipids in the bilayer, i.e., lipid photochemistry; the photo induced change in the association of polyelectrolytes with liposomes; and the photoinitiated polymerization of some or all of the lipids in the liposome, i.e., photopolymerization. A characteristic of photopolymerization processes is their multiplicative nature, which generally results in a greater perturbation of the bilayer membrane for equivalent light exposures. An extensive review of methods to photochemically reorganize lipid bilayers has been published (O'Brien et al., *Bioorganic Photochemistry* 1993, 2:111-167).

The photopolymerization of selected lipids in a multicomponent membrane can alter the lateral distribution of lipids within the bilayer to form domains enriched in polymerized lipids (Armitage et al., *Adv. Polym. Sci.* 1996, 126:53-85). It is known that processes that cause the phase separation of PE and other lipids can trigger lamellar to nonlamellar phase transition(s). The polymerization of two (or multi) component lipid bilayers, with one polymerizable and other nonpolymerizable component(s), can cause lipid domain formation. The polymerizable lipids form covalently linked domains as the reaction proceeds, which in turn produces domains of the nonpolymerizable component(s). Recently, O'Brien and coworkers showed that if the nonpolymerizable component prefers a nonlamellar rather than a lamellar structure the membrane will be destabilized (Lamparski et al., *Biochemistry* 1992, 31:685-694; Bennett et al., *Biochemistry* 1995, 34:3102-3113). Phosphatidylethanolamines (PE) are of particular interest because they form nonbilayer structures under physiological conditions. Two-component liposomes of a polymerizable PC and a PE form stable liposomes prior to polymerization, but are destabilized by photopolymerization of a bis-SorbPC which contains a photosensitive sorbyl moiety at the terminal end of each acyl chain. Consequently, the photopolymerization of properly designed lipid bilayers can initiate the localized destabilization of the bilayer, which is observed either as the leakage of encapsulated reagents (Lamparski et al., supra) or the fusion of bilayer liposomes (Bennett et al., supra).

These original studies utilized the native photosensitivity of the bis-SorbPC due to its chromophore at 260 nm. In principle, liposome destabilization can be achieved by the polymerization of a host of reactive lipids that are known in the literature. The polymerization of supramolecular assemblies of amphiphiles was first demonstrated in monolayers, vesicles, and extended bilayers. The introduction of synthetic double tail amphiphiles coupled with the successful demonstration of polymerization of fatty acid monolayers led directly to the description of a cationic ammonium salt with a methacrylate at the end of one hydrocarbon chain in the early 1980s. Reports of the syntheses and polymerization of lipid diacetylenes in bilayers followed. Further, syntheses and polymerization of dienoyl lipids, additional methacryloyl lipids, other lipid diacetylenes, and vinyl lipids appeared as well (Ringsdorf et al., *J. Angew. Chem. Int. Ed. Engl.* 1988, 27:113-158; O'Brien et al., *Encylopedia Polym. Sci. Engr.* 1989, 17:108-135; O'Brien et al., *Acc. Chem. Res* 1998, 31:861-868). The polymerization of these reactive lipids in a self-organized array of several thousand lipid molecules into a structure that contains several polymer chains is termed the formation of polymerized liposomes.

Figure 1:
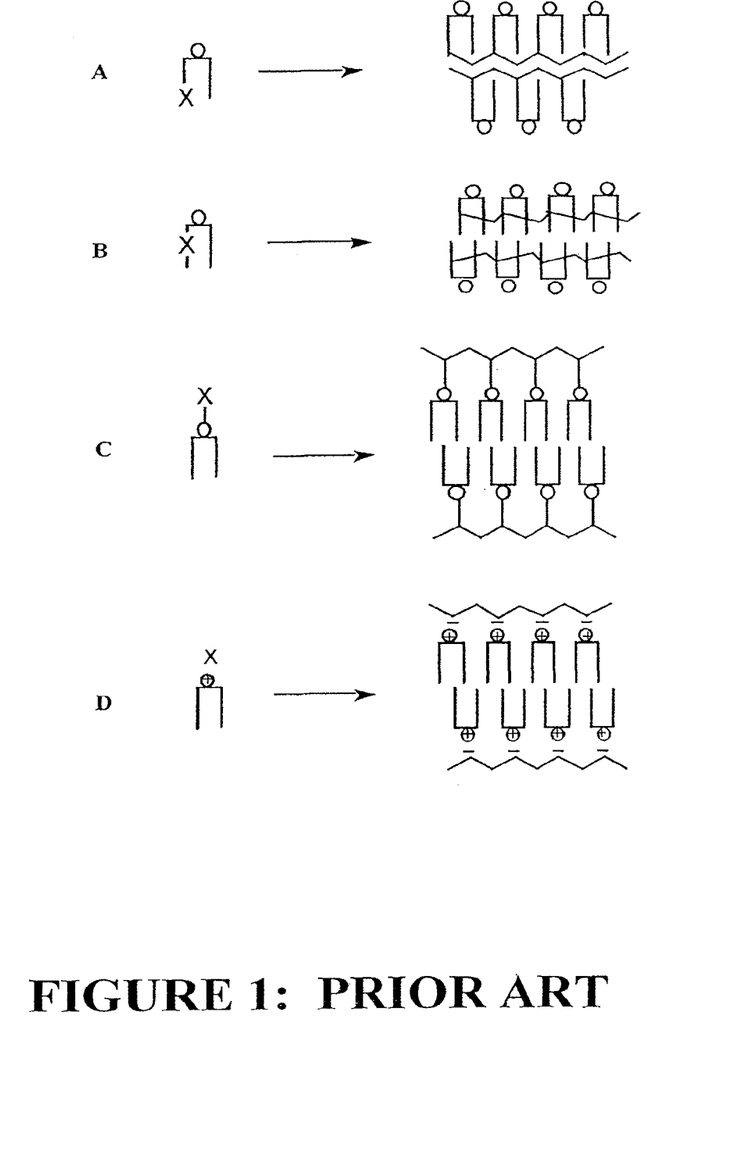
FIG. 1 provides a schematic representation of polymerizable lipids well known in the art. The circle in each icon represents the hydrophilic part of the molecule. The hydrophobic region is represented by the line(s). The polymerizable group X may be at the chain terminus in the middle of the bilayer (type A), near the middle of the hydrophobic chains (type B), attached to the hydrophilic head group (type C), or electrostatically associated with a charged lipid (type D).

A major strategy for the formation of polymerized bilayers and other supramolecular assemblies is the preparation of polymerizable lipid monomers, the formation of the lipid assembly such as bilayer membranes from the monomer, and the subsequent chain polymerization of the monomers in the assembly. Polymerizable lipids have been prepared by introduction of the reactive group into different regions of the lipid molecule. A schematic representation of these types of polymerizable lipids is shown in FIG. 1. As shown in FIG. 1, polymerization strategies A and B have no direct influence on the membrane-water interface. The mobility of the lipid chains is significantly decreased by polymerization in these systems. In contrast methods C and D alter the membrane-water interface, but have less effect on the hydrophobic interior of the membrane. These examples with only one reactive group per lipid form linear polymer chains in supramolecular assemblies. The presence of a second polymerizable group per molecule (not shown) allows crosslinking of the polymer chains.

A host of reactive moieties have been utilized to modify the above lipids to make them polymerizable. These groups include diacetylene, acryloyl, methacryloyl, itaconyl, dienoyl, sorbyl, muconyl, styryl, vinyl, thiol (or lipoyl), and chain terminal isocyanates. Systematic studies of the relationship between polymer chain length, i.e., degree of polymerization ($X_n$), and the molar ratio of monomer to initiator revealed that $X_n$ was proportional to [M]/[I]. Moreover, these studies showed that the relative reactivity of monomers in bilayer membranes is similar to values obtained from the multitude of solution polymerization studies. Consequently, an acryloyl lipid monomer in a bilayer is four to five times more reactive than a diene containing lipid monomer.

Polymerization of lipids in bilayer membranes can be caused by various methods, including photo, thermal, and redox initiation. Diacetylenic, butadienic, vinylic, acryloylic, methacryloylic, and thiolic units have been used as polymerizable units in acyl chains. However, while the use of ionizing radiation to initiate chain polymerizations is known in the art, less is known about the effects of ionizing radiation in order to stabilize lipid bilayer membranes composed of polymerizable lipids. Akama et al. report the stabilization of liposomes by the polymerization of polymerizable phospholipids contained in the membrane. More specifically, they report stabilization of liposomes as a result of polymerization by hydroxyl radicals generated by gamma-irradiation. The design of polymerizable phospholipids is important for obtaining a stabilizable liposome by polymerization (Akama et al., *J. Mater. Chemistry* 2000, 10:1047-1059). However, while the use of ionizing radiation to stabilize lipid bilayer membranes composed of polymerizable lipids is known, there are no reports about the use of ionizing radiation for the purpose of liposome destabilization.

The methods described above relating to radiant energy initiated polymerization of the lipid bilayer rely on ultraviolet light. The potential utility of polymerizable liposomes for drug delivery, diagnostics, and reagent release is limited if only ultraviolet light can be used for initiation of polymerization. UV light can only be used where the target tissue is superficially accessible to the light source. Liposomes that exist at deeper tissue levels would not be accessible to UV light and liposome-encapsulated or associated diagnostic or therapeutic agents could therefore not be released. Hence, a better system is required to achieve destabilization of liposomes. All publications, patents, and other reference materials referred to herein are incorporated herein by reference.

SUMMARY OF THE INVENTION

The present invention relates to liposome(s) that are radiation sensitive and methods of producing them. The present invention further encompasses methods of diagnosing and treating conditions and diseases that are responsive to liposome-encapsulated or associated agents.

One aspect of the present invention provides a liposomal delivery system, comprising a stable liposome-forming lipid and a polymerizable colipid, a fraction of which polymerizable colipid polymerizes upon exposure to ionizing radiation, thereby destabilizing the liposomal membrane. More specifically, the radiation sensitive liposome of the instant invention comprises polymerizable colipid(s) in the liposomal membrane which polymerize upon exposure to ionizing radiation, destabilizing the liposomal membrane and allowing leakage of liposomal contents. In particular, a radiation sensitive liposome that forms discrete domains of polymerizable colipid(s) is encompassed by the present invention. The domains polymerize upon exposure to ionizing radiation, thereby allowing leakage of liposomal contents through or around the polymerized domains. In another embodiment, the radiation sensitive liposome comprises polymerizable colipid(s) that are randomly distributed throughout the liposomal membrane. These lipid(s) polymerize upon exposure to ionizing radiation, thereby allowing leakage of liposomal contents throughout the liposome. Thus, destabilization of liposome(s) can be achieved by polymerization of reactive colipid(s) in the lipid bilayers of the liposome(s). The use of ionizing radiation to release liposomal contents of diagnostic and therapeutic nature provides an efficient and convenient means of diagnosing and treating cancer and other diseases, due to its ease of integration into currently available radiation based clinical methods.

In a preferred embodiment, the radiation sensitive liposome(s) include sterically stabilized liposome(s) having components such as a poly(ethylene glycol) (PEG) or other hydrophilic polymers that confer steric stabilization; lipids; and polymerizable colipids. Examples of lipids include, but are not limited to, phosphatidylcholine (PC), phosphatidylethanolamine (PE), phosphatidic acid (PA), phosphatidylglycerol (PG), sterol such as cholesterol, nonnatural lipid(s), and cationic lipid(s). Examples of polymerizable colipids include, but are not limited to, mono-lipids with polymerizable moieties, bis-lipids with polymerizable moieties, and mixtures of mono- and bis-lipids with polymerizable moieties. More specifically, polymerizable colipid(s) include, but are not limited to, mono-, bis-, and heterobifunctional, diacetylenyl, acryloyl, methacryloyl, dienoyl, dienyl, sorbyl, muconyl, styryl, vinyl, and lipoyl colipid(s).

Another aspect of the present invention provides for radiation sensitive liposome(s) comprising polymerizable colipids including, but not limited to, bis-SorbPC, mono-SorbPC, bis-DenPC, mono-DenPC, bis-AcrylPC, mono-AcrylPC, bis-MethacrylPC, mono-MethacrylPC, bis-VinylesterPC, mono-VinylesterPC, HeterobifunctionalPC, DiacetylenePC, MuconatePC; bis-SorbPE, mono-SorbPE, bis-DenPE, mono-DenPE, bis-AcrylPE, mono-AcrylPE, bis-MethacrylPE, mono-MethacrylPE, bis-VinylesterPE, mono-VinylesterPE, HeterobifunctionalPE, DiacetylenePE, MuconatePE; bis-SorbPG, mono-SorbPG, bis-DenPG, mono-DenPG, bis-AcrylPG, mono-AcrylPG, bis-MethacrylPG, mono-MethacrylPG, bis-VinylesterPG, mono-VinylesterPG, HeterobifunctionalPG, DiacetylenePG, MuconatePG; bis-SorbPA, mono-SorbPA, bis-DenPA, mono-DenPA, bis-AcrylPA, mono-AcrylPA, bis-MethacrylPA, mono-MethacrylPA, bis-VinylesterPA, mono-VinylesterPA, HeterobifunctionalPA, DiacetylenePA, and MuconatePA. Examples of heterobifunctional lipids are dienoyldienyl, dienoylsorbyl, and dienoylacryloyl. Examples of Heterobifunctional PC are dienoylsorbylPC (DenSorbPC) and dienoylacrylPC (DenAcrylPC). Polymerizable moieties may be incorporated into the lipid chains.

In one embodiment of the instant invention, the radiation sensitive liposome is a poly(ethylene glycol) (PEG) liposome. The attachment of PEG to lipid(s) in the liposome increases the period of circulation of the liposome in vivo. Examples of PEG liposome compositions are various combinations of PEG and PCs, and/or PEs, and/or PAs, and/or PGs, and/or sterols such as cholesterol, and/or nonnatural lipids, and/or cationic lipids. In a preferred embodiment of the instant invention, the liposome(s) are comprised of $PEG_{2000}$-dioleoylPE, cholesterol, dioleoylPC, and bis-$SorbPC_{17,17}$. In another preferred embodiment of the instant invention, the liposome(s) are comprised of $PEG_{2000}$-distearoylPE, cholesterol, distearoylPC, and bis-$SorbPC_{17,17}$. In yet another preferred embodiment of the instant invention, the liposome(s) are comprised of $PEG_{2000}$-distearoylPE, distearoylPC, and bis-$SorbPC_{17,17}$.

Another aspect of the present invention provides for a liposomal delivery system, wherein the liposome comprises a releasable agent. Examples of releasable agent(s) are liposome-encapsulated or associated molecules. Such encapsulated molecules may be water soluble molecules. Alternatively, liposome(s) may comprise lipid associated molecules. The releasable agent(s) include, but are not limited to; therapeutic agents and diagnostic agents. Examples of therapeutic agents include, but are not limited to, chemotherapeutics, biological response modifiers, biological cofactors, pharmaceuticals and radiopharmaceuticals, cell toxins, radiation sensitizers, and genetic materials. Examples of diagnostic agents include, but are not limited to, contrast agents, iodinated agents, radiopharmaceuticals, fluorescent compounds and fluorescent compounds coencapsulated with a quencher, agents containing MRS/MRI sensitive nuclides, and genetic material encoding contrast agents.

Therapeutic doses of ionizing radiation can substantially enhance the release of encapsulated water soluble molecules or lipid associated molecules from the liposome(s). Thus, these conditions are suitable for the destabilization of sterically stabilized liposomes, particularly for therapeutic and diagnostic purposes.

The present invention also encompasses a pharmaceutical composition comprising a liposomal delivery system and releasable agent, wherein the releasable agent is encapsulated in or associated with the liposome(s). The pharmaceutical composition may include or be associated with an additional suitable pharmaceutical carrier or diluent. The releasable agent may be a therapeutic or diagnostic agent. Carrying a therapeutic or diagnostic agent within or associated with a liposome provides for a biocompatible and non-toxic means of in vivo delivery. Chemotherapeutics, biological response modifiers, biological cofactors, pharmaceuticals and radiopharmaceuticals, cell toxins, radiation sensitizers, genetic materials, contrast agents, iodinated agents, fluorescent compounds and fluorescent compounds coencapsulated with a quencher, agents containing MRS/MRI sensitive nuclides, genetic material encoding contrast agents, and the like, may be encapsulated in or associated with the liposome(s) of the instant invention and released at desired target sites in vivo or in vitro. The liposome(s) can be formulated to include a variety of compositions and structures that are potentially non-toxic, degradable, and nonimmunogenic.

In another embodiment, the instant invention provides for a method of treating a condition responsive to a liposome-encapsulated or associated therapeutic agent, comprising the steps of (i) administering to a patient a pharmaceutical composition comprising a liposomal delivery system and releasable agent such as a therapeutic agent, wherein the releasable agent is encapsulated in or associated with the liposome, and a pharmaceutically acceptable carrier or diluent; and (ii) subjecting the patient to radiation in order to destabilize the liposome and release the therapeutic agent encapsulated in or associated with the liposome. In one embodiment, the radiation dosage ranges from about 5 to about 500 rads. In a preferred embodiment, the radiation dosage ranges from about 50 to about 250 rads. Examples of therapeutic agents include, but are not limited to, chemotherapeutics, biological response modifiers, biological cofactors, pharmaceuticals and radiopharmaceuticals, cell toxins, radiation sensitizers, and genetic materials. Examples of conditions that are responsive to liposome-encapsulated or associated therapeutic agent(s) include, but are not limited to, cancer, immune disorders, developmental disorders, and genetic disorders.

In still another embodiment, the instant invention provides for a method of diagnosing the presence or progression of a disease, comprising the steps of (i) administering to a patient a pharmaceutical composition comprising a liposomal delivery system and releasable agent such as a diagnostic agent, wherein the releasable agent is encapsulated in or associated with the liposome, and a pharmaceutically acceptable carrier or diluent; (ii) subjecting the patient to ionizing radiation in order to destabilize the liposome and release the diagnostic agent encapsulated in or associated with the liposome; and (iii) diagnosing the disease through use of molecular imaging techniques. In one embodiment, the radiation dosage ranges from about 5 to about 500 rads. In a preferred embodiment, the radiation dosage ranges from about 50 to about 250 rads. Examples of diagnostic agents include, but are not limited to, contrast agents, iodinated agents, radiopharmaceuticals; fluorescent compounds and fluorescent compounds coencapsulated with a quencher, agents containing MRS/MRI sensitive nuclides, and genetic material encoding contrast agents. Examples of molecular imaging techniques include, but are not limited to, Nuclear Magnetic Resonance (NMR), Magnetic Resonance Spectroscopy/Magnetic Resonance Imaging (MRS/MRI), X-ray/computed axial tomography (CT), Positron Emission Tomography (PET), Single-photon Emission Computed Tomography (SPECT), ultrasound, and optical based imaging techniques. Examples of conditions that can be diagnosed via liposome-encapsulated or associated diagnostic agent(s) include, but are not limited to; cancer, immune disorders, developmental disorders, and genetic disorders.

Yet, another embodiment of the present invention provides for a method of producing a radiation sensitive liposome comprising polymerizable colipid(s). The method encompasses drying the lipids that comprise the liposome(s), hydrating the lipids with a buffer comprising agents to be encapsulated or associated in a desired molar ratio to create hydrated bilayers, converting the bilayers into liposome(s), and purifying the liposome(s). Preferably, the lipids are dried in an oxygen free environment, such as an argon stream, and the bilayers are converted into liposomes by ultrasonification or freeze-thawing-extrusion. The liposomes may be purified with gel permeation chromatography or other methods.

The present invention further contemplates a liposomal delivery system comprising a radiation sensitive liposome and releasable agent that can be targeted to a tumor site through attachment of at least one peptide to the liposome. The liposome comprises polymerizable colipid(s) in the liposomal membrane, a fraction of which polymerize upon exposure to ionizing radiation, thereby destabilizing the liposomal membrane. This allows for leakage of liposomal contents. Peptides that target liposome(s) to tumor sites include, but are not limited to, peptide sequences, peptide fragments, antibodies, antibody fragments, and antigens.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The present invention is best understood when read in conjunction with the accompanying figures that serve to illustrate the preferred embodiments. It is understood, however, that the invention is not limited to the specific embodiments disclosed in the figures.

DETAILED DESCRIPTION OF THE INVENTION a) Definitions and General Parameters

The following definitions are set forth to illustrate and define the meaning and scope of the various terms used to describe the invention herein.

The term "liposome" refers to a microscopic vesicle comprising lipid bilayer(s). Structurally, liposomes range in size and shape from long tubes to spheres and are normally 100±10 nm in diameter; but can be as small as 25 nm and as large as 500 nm in diameter. Liposomes may contain one or more bilayer(s). Agents or molecules can be incorporated into the liposome. For example, molecules may be encapsulated in or associated with the liposome. A liposome with such encapsulated or associated agents (e.g., therapeutic or diagnostic agents) may be targeted to specific site(s) (e.g., tissue of interest such as a tumor tissue) and its contents released when appropriate. Liposomes may also be targeted to specific site(s) in vitro or in vivo through attached targeting sequences such as peptide sequences or the like.

The term "lipid", as referred to herein, means a long-chain molecule comprised of fatty acids that may form liposomes under suitable liposome forming conditions. Examples of such lipids include, but are not limited to, phosphatidylcholine (PC), phosphatidylethanolamine (PE), phosphatidic acid (PA), phosphatidylglycerol (PG), sterol such as cholesterol, and nonnatural lipid(s) and cationic lipid(s) such as DOTMA (N-(1-(2,3-dioxyloxy)propyl)-N,N,N-trimethyl ammonium chloride).

A "polymerizable colipid", as used herein, is any lipid that has at least one polymerizable moiety incorporated into its lipid chain(s) anywhere in the chain(s). If more than one polymerizable moiety is incorporated into the lipid chain(s), then the incorporated polymerizable moieties may be of the same or different type. For example, a polymerizable colipid may include two polymerizable moieties, such as a sorbyl and a dienoyl group, in the same colipid. Ionizing radiation polymerizes at least a fraction of the polymerizable colipids in the liposomal membrane causing leakage of encapsulated or associated agents from the liposome. For example, after about 5% of polymerizable lipids are polymerized leakage of liposomal contents may occur. Alternatively, after about 10% of polymerizable lipids are polymerized leakage of liposomal contents may occur. However, no limitation with respect to the amount of polymerization and polymerization rate is suggested. The amount of leakage of encapsulated or associated agents in any given liposome depends on the nature of the liposome (e.g., the liposome composition, the location of the reactive, group, the nature of the reactive group, etc.) as well as the type and strength of polymerization employed (e.g., ionizing radiation).

The term "discrete domains of polymerizable colipids" means, for the purpose of the specification and claims, polymerizable colipids clustered together into groups of various sizes in mono- and bilayers. These domains may introduce latent instability sites into the liposome. Since lipids can form immiscible mixtures of reactive and nonreactive lipids, the "discrete domains of polymerizable colipids" may exist as groups of only reactive lipids or mixtures of reactive and nonreactive lipids. Ionizing radiation polymerizes the "discrete domains of polymerizable colipids", causing shrinkage of the domains and leakage of encapsulated or associated agents from the liposome.

"Genetic materials", as referred to herein, encompass chromosome(s), DNA, cDNA, genomic DNA, mRNA, polynucleotide(s), oligonucleotide(s), nucleic acid(s), and any synthetic DNA and RNA sequences, comprising the natural nucleotide bases adenine, guanine, cytosine, thymine, and uracil. The term also encompasses sequences having one or more modified nucleotides. The term further includes sense and antisense nucleic acids. No limitation as to length or to synthetic origin are suggested by the use of either of these terms herein.

The term "peptide" as used herein, refers to one amino acid or a poly(amino acid) such as a polypeptide comprising at least two amino acids linked by peptide bonds. The term further encompasses a peptide fragment, epitope, protein fragment, antigen, antibody, antibody fragment, or any amino acid sequence. A protein is a polypeptide which is encoded by a gene.

b) Radiation Sensitive Liposomes

The instant invention describes the use of ionizing radiation to polymerize lipids in a manner that destabilizes liposomes and causes the release of their encapsulated or associated contents at specific target sites. This method has distinct advantages over photoinitiated release. First, and most importantly, ionizing radiation is not limited by the depth of penetration as is radiant energy. Ionizing radiation can penetrate even the deepest of tissue sites. Secondly, the use of ionizing radiation as a standard treatment for various conditions and diseases relies on sources that are readily available (e.g., radiation treatment in hospitals and clinics). Furthermore, dosimetry for radiation treatment has already been carefully determined in the art which establishes immediate applicability. In summary, the present invention provides a novel system and methods for the release of liposome-encapsulated or associated diagnostic or therapeutic agents. Hence, radiation sensitive liposomes are particularly suitable for diagnosing and treating conditions and diseases that are responsive to liposome-encapsulated or associated agents, such as cancer, immune disorders, developmental disorder, genetic disorder, and the like.

Lipid assemblies, such as liposomes, are arrays of noncovalently associated amphiphiles, i.e., supramolecular assemblies. They can be classified as supported or self-supported assemblies. The polymerization of liposomes can lock in preexisting lipid domains or create lipid domains from random mixtures, depending on the nature of the polymerizable amphiphile. Lipids can form an unpolymerized immiscible mixture of reactive and nonreactive lipids in mono- and bilayers. In contrast, polymerization of polymerizable colipids can effectively induce the phase separation of unreactive lipids from the growing polymeric domains. Hence, lipid domains can endow liposomes with latent instability sites. Therapeutic doses of ionizing radiation can then substantially enhance the release of encapsulated water soluble or lipid associated molecules from radiation sensitive liposomes. These conditions are suitable for the destabilization of radiation sensitive liposomes that are optionally sterically stabilized.

One aspect of the present invention provides a liposomal delivery system, comprising a stable liposome-forming lipid and a polymerizable colipid, a fraction of which polymerizable colipid polymerizes upon exposure to ionizing radiation, thereby destabilizing the liposomal membrane. More specifically, the radiation sensitive liposome of the instant invention comprises polymerizable colipid(s) in the liposomal membrane which polymerize upon exposure to ionizing radiation, destabilizing the liposomal membrane and allowing leakage of liposomal contents. In particular, a radiation sensitive liposome that forms discrete domains of polymerizable colipid(s) is encompassed by the present invention. The domains polymerize upon exposure to ionizing radiation, thereby allowing leakage of liposomal contents through or around the polymerized domains. In another embodiment, the radiation sensitive liposome comprises polymerizable colipid(s) that are randomly distributed throughout the liposomal membrane. Radiation causes the polymerization of polymerizable colipid(s) that are clustered in discrete domains or are randomly distributed throughout the liposomal membrane in a manner that destabilizes the liposome(s) and thereby causes the release of their encapsulated or associated contents. Thus, destabilization of liposome(s) can be achieved by polymerization of reactive colipid(s) in the lipid bilayers of the liposome(s).

Figure 2:
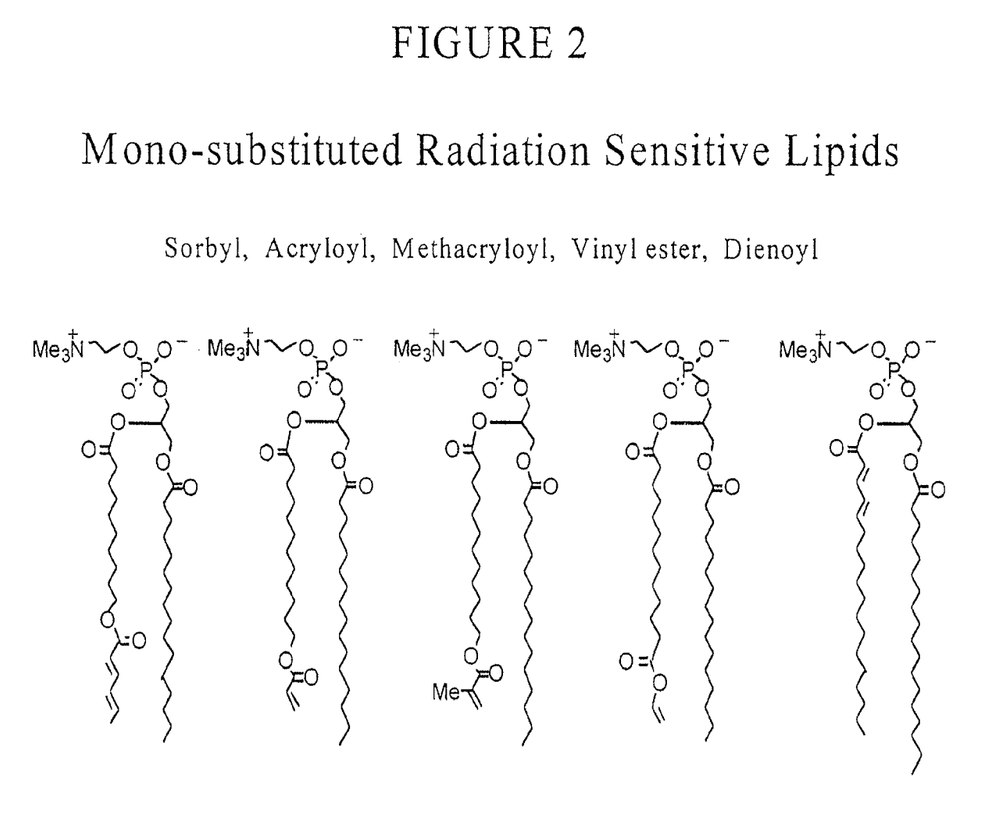
FIG. 2 depicts the structures of mono-substituted polymerizable phosphatidylcholines with various reactive groups to illustrate the instant invention. The lipid chain length and/or head group can be varied.
Figure 3:
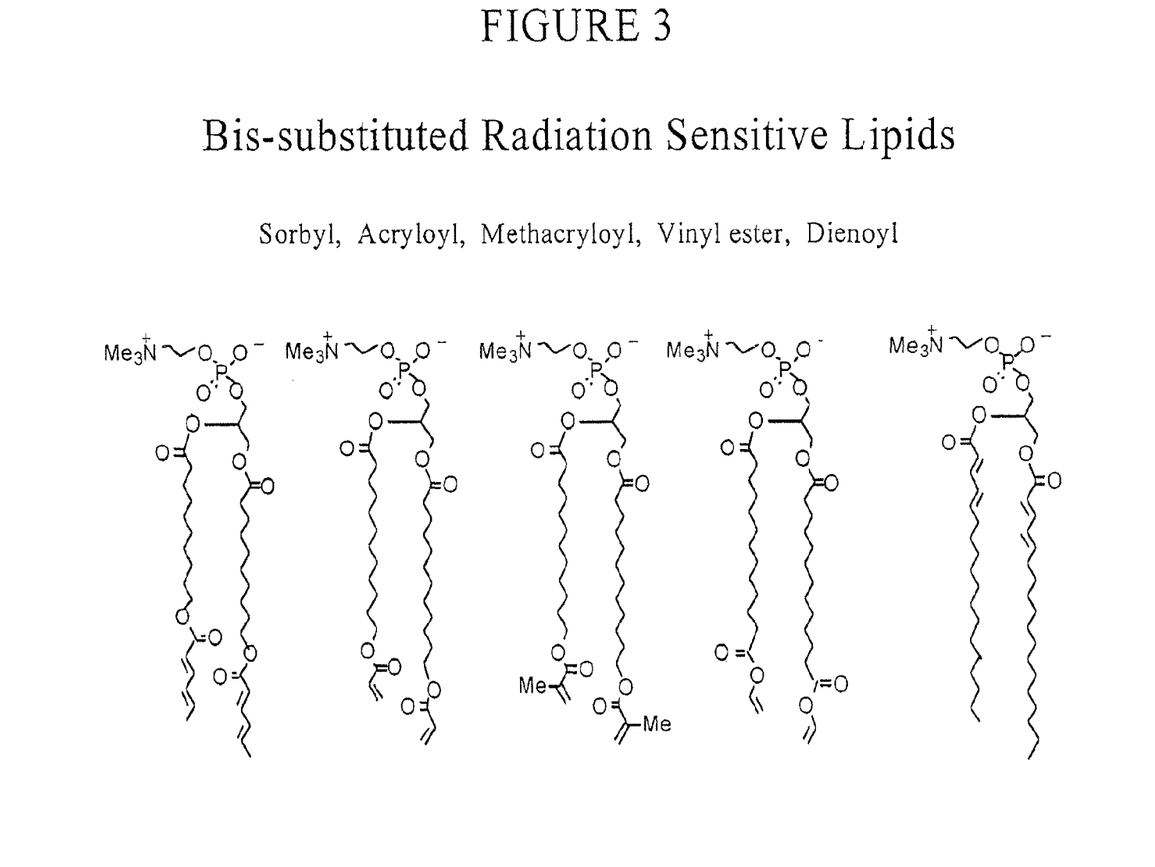
FIG. 3 depicts the structures of bis-substituted polymerizable phosphatidylcholines with various reactive groups to illustrate the instant invention. The lipid chain length and/or head group can be varied.

In a preferred embodiment, the radiation sensitive liposome(s) include sterically stabilized liposome(s) having components such as a poly(ethylene glycol) (PEG) or other hydrophilic polymers that confer steric stabilization; lipids; and polymerizable colipids. Examples of lipids include, but are not limited to, phosphatidylcholine (PC), phosphatidylethanolamine (PE), phosphatidic acid (PA), phosphatidylglycerol (PG), sterol such as cholesterol, and nonnatural lipid(s) and cationic lipid(s) such as DOTMA. Examples of polymerizable colipids include, but are not limited to, mono-lipids with polymerizable moieties, bis-lipids with polymerizable moieties, and mixtures of mono- and bis-lipids with polymerizable moieties. More specifically, polymerizable colipid(s) include, but are not limited to, mono-, bis-, and heterobifunctional, diacetylenyl, acryloyl, methacryloyl, dienoyl, dienyl, sorbyl, muconyl, styryl, vinyl, and lipoyl colipid(s) (see FIGS. 2, 3, and 4). Heterobifunctional colipids include, but are not limited to, dienoyl dienyl, dienoyl sorbyl, and dienoyl acryloyl colipids (see FIG. 4).

Figure 4:
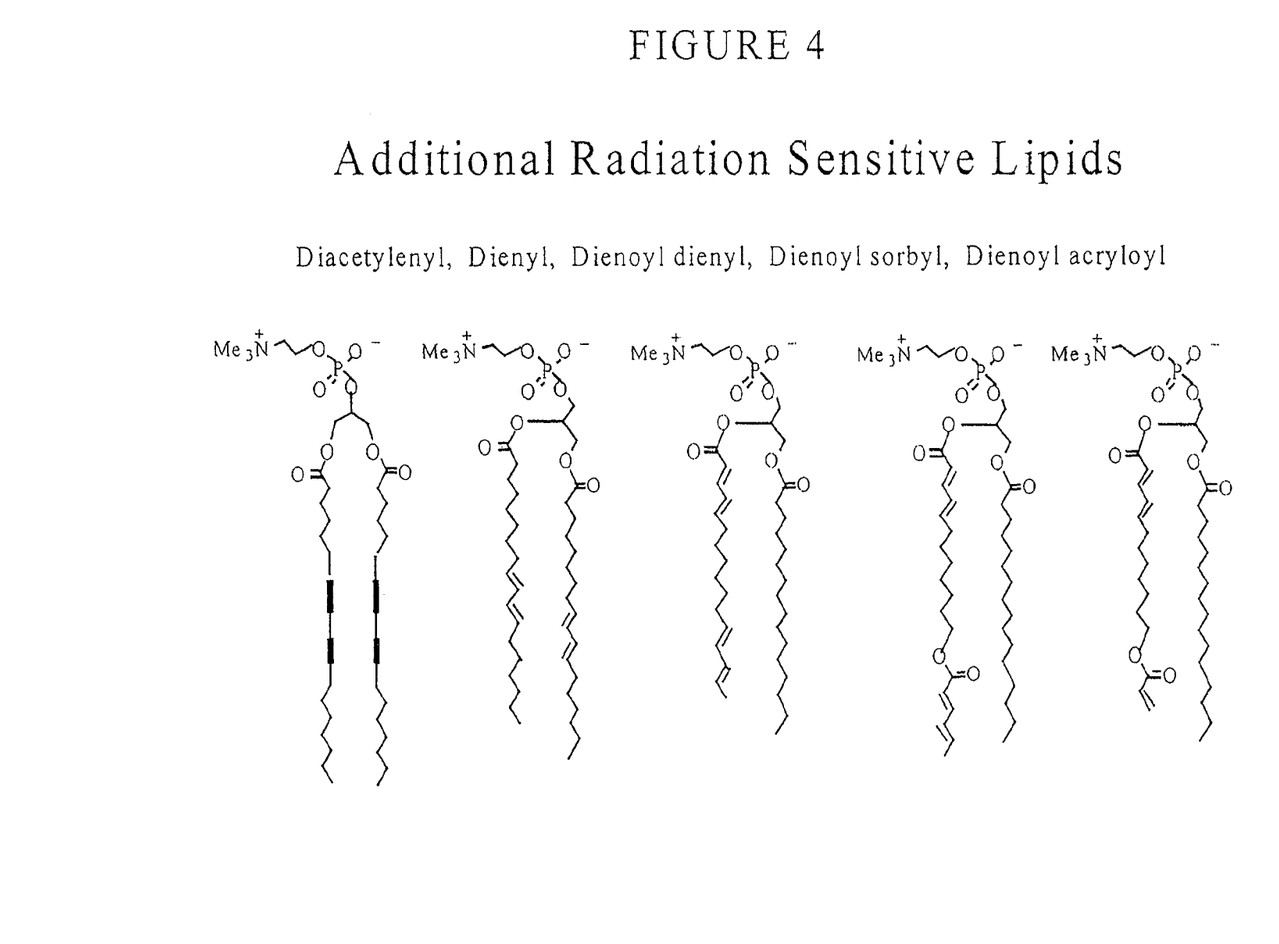
FIG. 4 shows the structures of additional polymerizable lipids, including examples of heterobifunctional lipids such as dienoyl dienyl, dienoyl sorbyl, and dienoyl acryloyl.
Figure 5:
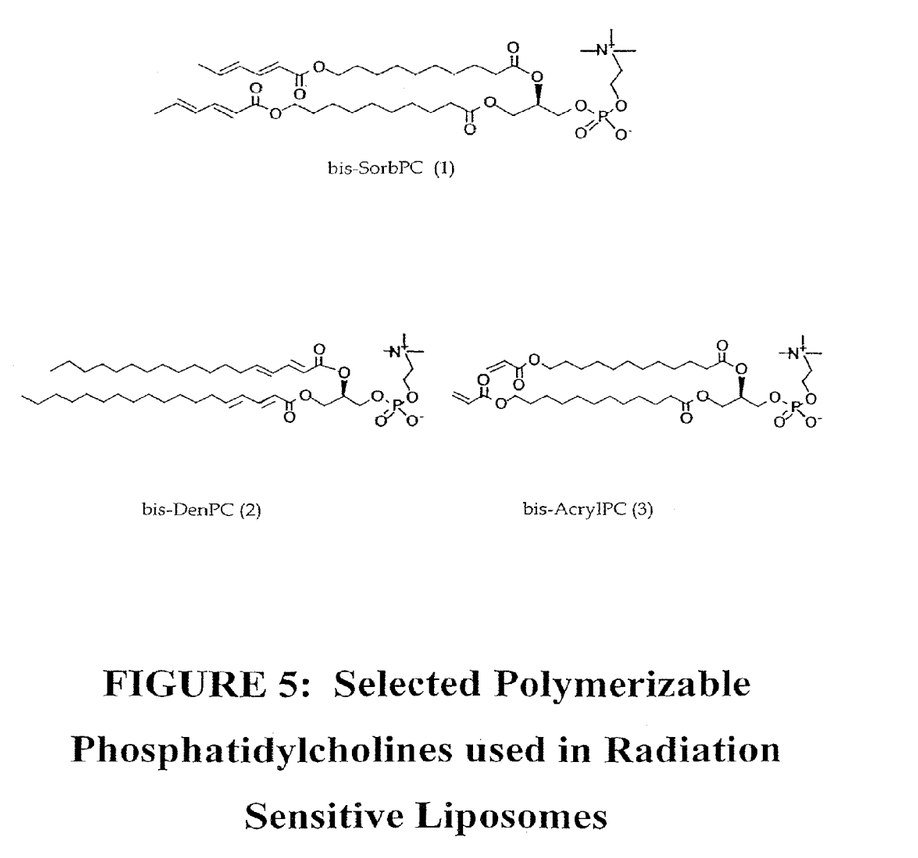
FIG. 5 shows examples of polymerizable phosphatidylcholines used in the liposomes of the instant invention, such as bis-SorbPC, bis-DenPC, and bis-AcrylPC.

Polymerizable moieties may be incorporated into the lipid chains (see FIGS. 4 and 5). For example, bis-SorbPC and mono-SorbPC have at least one polymerizable sorbyl moiety associated with the end of both or only one of their lipid chains, respectively (see FIGS. 2 and 3). Bis-DenPC contains at least one polymerizable dienoyl moiety, while bis-AcrylPC contains at least one reactive acryloyl moiety (see FIG. 5). Alternatively, a polymerizable colipid may include two different polymerizable moieties, such as sorbyl and dienoyl group, in the same colipid. The composition of the liposomes may vary, for example, the liposomes may include from about 5% to about 40% polymerizable colipids. In another example, the liposomes may include from about 2% to about 20% steric stabilizer. In still another example, the liposomes may include from about from about 5% to about 0.40% polymerizable colipids and from about 2% to about 20% steric stabilizer.

Another embodiment of the present invention provides for radiation sensitive liposomes comprising polymerizable colipids including, but not limited to, bis-SorbPC, mono-SorbPC, bis-DenPC, mono-DenPC, bis-AcrylPC, mono-AcrylPC, bis-MethacrylPC, mono-MethacrylPC, bis-VinylesterPC, mono-VinylesterPC, HeterobifunctionalPC, DiacetylenePC, MuconatePC; bis-SorbPE, mono-SorbPE, bis-DenPE, mono-DenPE, bis-AcrylPE, mono-AcrylPE, bis-MethacrylPE, mono-MethacrylPE, bis-VinylesterPE, mono-VinylesterPE, HeterobifunctionalPE, DiacetylenePE, MuconatePE; bis-SorbPG, mono-SorbPG, bis-DenPG, mono-DenPG, bis-AcrylPG, mono-AcrylPG, bis-MethacrylPG, mono-MethacrylPG, bis-VinylesterPG, mono-VinylesterPG, HeterobifunctionalPG, DiacetylenePG, MuconatePG; bis-SorbPA, mono-SorbPA, bis-DenPA, mono-DenPA, bis-AcrylPA, mono-AcrylPA, bis-MethacrylPA, mono-MethacrylPA, bis-VinylesterPA, mono-VinylesterPA, HeterobifunctionalPA, DiacetylenePA, and MuconatePA. Examples of heterobifunctional lipids are dienoyl dienyl, dienoyl sorbyl, and dienoyl acryloyl (see FIG. 4). Examples of HeterobifunctionalPC are dienoylsorbylPC (DenSorbPC) and dienoylacrylPC (DenAcrylPC).

More specifically, one embodiment of the instant invention describes the use of ionizing radiation in order to polymerize colipids clustered in discrete domains in a manner that destabilizes the liposomes and thereby causes leakage of their encapsulated contents such as therapeutic or diagnostic agents, wherein the leakage between or around domain boundaries is due to the shrinkage of domains. In an alternative embodiment, polymerizable colipids are randomly distributed throughout the liposomal membrane. Upon exposure to ionizing radiation these lipids polymerize and allow leakage of liposomal contents throughout the liposome. Hence, destabilization can be achieved by polymerization of reactive colipids in the lipid bilayers of the liposomes. Polymerizable colipids have different reactivities that control the initial rate of polymerization, extent of polymerization, and inhibition by oxygen. The interaction of ionizing radiation with water produces radical species that can initiate radical chain polymerizations. The use of ionizing radiation to rigger release of liposomal contents at the target site(s) in vivo or in vitro has several distinct advantages. Most importantly, ionizing radiation is not limited by the depth of penetration or the thickness of the specimen since it can penetrate through all layers of tissue. Furthermore, the use of ionizing radiation provides an efficient and convenient means of treating cancer and other diseases, due to its ease of integration into currently available radiation based clinical methods.

In one embodiment of the instant invention, the radiation sensitive liposome is a poly(ethylene glycol) (PEG) liposome. The attachment of PEG to lipids in the liposome increases the period of circulation of the liposome in vivo. Examples of PEG-liposome compositions are various combinations of PEG and PCs, and/or PEs, and/or PAs, and/or PGs, and/or sterols such as cholesterol, and/or nonnatural lipids, and/or cationic lipids. In a preferred embodiment of the instant invention, the liposomes are comprised of $PEG_{2000}$-dioleoylPE, cholesterol, dioleoylPC, and bis-$SorbPC_{17,17}$. In another preferred embodiment of the instant invention, the liposomes are comprised of $PEG_{2000}$-distearoylPE, cholesterol, distearoylPC, and bis-$SorbPC_{17,17}$. In yet another preferred embodiment of the instant invention, the liposome(s) are comprised of $PEG_{2000}$-distearoylPE, distearoylPC, and bis-$SorbPC_{17,17}$. Specific examples of PEG-liposomes include, but are not limited to, PEG-liposomes with a molar ratio of about 15% $PEG_{2000}$-dioleoylPE, 40% cholesterol, 20% dioleoylPC, and 30% bis-$SorbPC_{17,17}$; PEG-liposomes with a molar ratio of about 15% $PEG_{2000}$-distearoylPE, 40% cholesterol, 20% distearoylPC, and 30% bis-$SorbPC_{17,17}$; and PEG-liposomes with a molar ratio of about 5% $PEG_{2000}$-distearoylPE, 75% distearoylPC, and 20% bis-$SorbPC_{17,17}$ (vide infra).

Therapeutic doses of ionizing radiation can substantially enhance the release of encapsulated water soluble or lipid associated molecules from radiation sensitive liposomes. These conditions are suitable for the destabilization of radiation sensitive liposomes that are sterically stabilized. The enhanced depth of penetration of ionizing radiation is particularly suitable for therapeutic purposes. Moreover, because most medical centers have experience with focused ionizing radiation, the radiation induced destabilization of liposomes offers a spatially and temporally selective method to deliver and release agents for medical therapy and diagnostics.

The delivery of liposomes to desired anatomical sites depends in part on long liposome circulation times, which can be achieved if the liposomes are sterically stabilized by tethered hydrophilic polymers, such as PEG-PE. The increased permeability of the vasculature at tumor sites allows PEG-liposomes to escape the capillaries to reach the tumor interstitial space. However, once the PEG-liposomes are at the tumor site the PEG groups can interfere with rapid release of the encapsulated reagents. Consequently, it is a continuing challenge to find methods to trigger the release of reagents from PEG-liposomes. The instant invention is the first successful demonstration of the use of ionizing radiation to destabilize liposomes, including PEG-liposomes. Liposomes can be made radiation sensitive by the use of uniquely designed lipids (e.g., polymerizable colipids) that can alter the liposome properties. The proper choice of reactive lipids makes it possible to form crosslinked polymer networks in the bilayer that significantly alter bilayer properties. Thus, ionizing radiation can initiate the polymerization of lipid bilayers.

Another aspect of the present invention provides for a liposomal delivery system, wherein the liposome comprises a releasable agent. Examples of releasable agent(s) are liposome-encapsulated or associated molecules. Such encapsulated molecules may be water soluble molecules. Alternatively, liposome(s) may comprise lipid associated molecules. Hence, the liposome of the instant invention may comprise a releasable agent that is a water soluble or lipid associated molecule. The releasable agent(s) include, but are not limited to, therapeutic agents and diagnostic agents. Examples of therapeutic agents include, but are not limited to, chemotherapeutics, biological response modifiers, biological cofactors; pharmaceuticals and radiopharmaceuticals, cell toxins, radiation sensitizers, and genetic materials. Examples of diagnostic agents include, but are not limited to, contrast agents, iodinated agents, radiopharmaceuticals, fluorescent compounds and fluorescent compounds coencapsulated with a quencher, agents containing MRS/MRI sensitive nuclides, and genetic material encoding contrast agents.

Radiation sensitive liposomes possess the ability to localize at tumor sites due to increased permeability of the vasculature near tumor associated areas. The release of encapsulated or associated agents from liposomes may occur passively or may be stimulated or induced. For example, ionizing radiation can stimulate the release of liposomal contents. Furthermore, liposomal delivery to target cells may be accomplished through leakage (passive or induced) or through endocytosis. In endocytosis, liposomes contact the cell membrane, form a vesicle within an endosome, and eventually fuse with other organelles to release their contents. Therapeutic doses of ionizing radiation substantially enhance the release of encapsulated water soluble molecules or lipid associated molecules from the liposomes. The enhanced depth of penetration of ionizing radiation overcomes the limitation of previous methods which rely on UV light to destabilize liposomes since UV light does not penetrate beyond the epidermal layer of the body. Thus, these conditions are suitable for the destabilization of radiation sensitive liposomes, particularly for therapeutic and diagnostic purposes.

The present invention also encompasses a pharmaceutical composition comprising a liposomal delivery system and releasable agent, wherein the releasable agent is encapsulated in or associated with the liposome(s). The pharmaceutical composition may include or be associated with an additional suitable pharmaceutical carrier or diluent. The releasable agent may be a therapeutic or diagnostic agent. Carrying a therapeutic or diagnostic agent within or associated with a liposome provides for a biocompatible and non-toxic means of in vivo delivery. Chemotherapeutics, biological response modifiers, biological cofactors, pharmaceuticals and radiopharmaceuticals, cell toxins, radiation sensitizers, genetic materials, contrast agents, iodinated agents, fluorescent compounds and fluorescent compounds coencapsulated with a quencher, agents containing MRS/MRI sensitive nuclides, genetic material encoding contrast agents, and the like, may be encapsulated in or associated with the liposome(s) of the instant invention and released at desired target sites in vivo or in vitro. The liposome(s) can be formulated to include a variety of compositions and structures that are potentially non-toxic, degradable, and nonimmunogenic. Liposomal drug delivery provides advantages over viral delivery and other methods such as greater biocompatibility, less toxicity, fewer side effects, and others. Furthermore, the addition of nucleic acid material to liposomes for therapeutic purposes may trigger structural changes in the liposomes as well as the DNA. The benefits associated with such structural changes are that the DNA molecule adopts a structure that renders the molecule partially protected from extracellular and intracellular degradation. Hence, the liposomes provide a targeting as well as a protective mechanism for the encapsulated nucleic acids.

The present invention further contemplates a liposomal delivery system comprising a radiation sensitive liposome and releasable agent that can be targeted to a tumor site through attachment of at least one peptide to the liposome.

The liposome comprises polymerizable colipid(s) in the liposomal membrane, a fraction of which polymerize upon exposure to ionizing radiation, thereby destabilizing the liposomal membrane. This allows for leakage of liposomal contents. Peptides that target liposome(s) to tumor sites include, but are not limited to, peptide sequences, peptide fragments, antibodies, antibody fragments; and antigens. Antibodies that are specific to tumor cells can be attached to a liposome which allows for selective targeting. Such antibodies can bind to selective antigens on the tumor cells which brings the liposome into close proximity of a tumor or malignant tissue. After binding of the antibody to the tumor antigen the liposome is linked to the tumor tissue. Ionizing radiation can then trigger the release of liposomal contents such as anti-tumor agents. Specific antigens may also be attached to the liposome. Such antigens may link attached liposomes to antibodies that are localized around tumor sites. Specific peptide sequences (e.g., epitopes) that bind to selective receptors may also be attached to the liposome, wherein any number of peptide sequences may be attached. The peptide sequence targets the liposome to a specific tissue. One or more peptides may be used to specifically target a liposome to a tumor tissue. One advantages of introducing several targeting peptides to the surface of the liposome is that, while the target affinity for a single peptide may be lower, the incorporation of multiple peptides into a liposome increases the overall likelihood of these peptides to bind to selective receptors on a tumor tissue.

c) Production of Radiation Sensitive Liposomes

Another embodiment of the present invention provides for a method of producing a radiation sensitive liposome comprising polymerizable colipid(s). The method encompasses drying the lipids that comprise the liposomes, hydrating the lipids with a buffer comprising agents to be encapsulated or associated in a desired molar ratio to create hydrated bilayers, converting the bilayers into liposomes, and purifying the liposomes. The encapsulated or associated agents include, but are not limited to, therapeutic and diagnostic agents.

The lipids that comprise the liposome may be dried in an oxygen free environment such as under an argon stream, followed by drying under vacuum and weighing. The lipids in the desired molar ratio are hydrated with a buffer including the agents to be encapsulated or associated. The hydrated bilayers can then be converted into liposomes by either ultrasonication, freeze/thawing and extrusion procedures, or other conventional liposome preparation procedures. In some instances it may be preferable to load the liposomes with therapeutic agents by using a pH gradient to drive weak bases, such as doxorubicin, into the liposomes. The liposomes may be purified by elution such as a gel permeation chromatography column with an isoosmotic buffer to remove unencapsulated or unassociated agents. Other purification methods can be used as well. The liposome size distributions can be measured by dynamic light scattering. The liposomes can also be imaged by electron microscopy. Liposomes are normally 100±10 nm in diameter, but can be as small as 25 nm and as large as 500 nm in diameter (vide infra).

The effect of polymerization on bilayer properties are a consequence of the design features of the polymerizable colipid, i.e., the location of the reactive group, the nature of the reactive group, as well as the type of polymerization employed. A variety of reactive moieties can be utilized to modify lipids to make them polymerizable. These groups include diacetylenyl, acryloyl, methacryloyl, dienoyl, dienyl, sorbyl, muconyl, styryl, vinyl, lipoyl, and the like (see FIGS. 2, 3, and 4). The polymerization of reactive lipids in a self-organized bilayer vesicle of several thousand lipid molecules into a structure that contains several polymer chains is termed the formation of polymerized liposomes. The most successful strategy for the formation of polymerized bilayer membranes is the preparation of polymerizable lipid monomers, the formation of the lipid bilayers from the monomer with or without other lipids, and the subsequent chain polymerization of the monomers in the assembly.

d) Treatment with Radiation Sensitive Liposomes

In one embodiment, the instant invention provides for a method of treating a condition responsive to a liposome-encapsulated or associated therapeutic agent, comprising the steps of (i) administering to a patient a pharmaceutical composition comprising a liposomal delivery system and releasable agent such as a therapeutic agent, wherein the releasable agent is encapsulated in or associated with the liposome, and a pharmaceutically acceptable carrier or diluent; and (ii) subjecting the patient to radiation in order to destabilize the liposome and release the therapeutic agent encapsulated in or associated with the liposome. In one embodiment, the radiation dosage ranges from about 5 to about 500 rads. In a preferred embodiment, the radiation dosage ranges from about 50 to about 250 rads. Examples of conditions that are responsive to liposome-encapsulated or associated therapeutic agent(s) include, but are not limited to, cancer, immune disorders, developmental disorders, and genetic disorders. Examples of therapeutic agents include, but are not limited to, chemotherapeutics, biological response modifiers, biological cofactors, pharmaceuticals and radiopharmaceuticals, cell toxins, radiation sensitizers, and genetic materials. Examples of chemotherapeutics include, but are not limited to, alkylating agents such as nitrogen mustards (e.g., chlorambucil, estramustine, mechlorethamine, melphalan); ethylenimine derivatives such as thiotepa; alkyl sulfonates such as busulfan; nitrosoureas such as carmustine (BCNU), lomustine (CCNU), methyl-CCNU, and streptozocin; triazines such as dacarbazine; metal salts such as cisplatin and carboplatin; antimetabolites; folic acid analogues such, as methotrexate; pyrimidine analogues such as 5-fluorouracil and floxuridine; purine analogues such as 6-mercaptopurine, 6-thioguanine, deoxycorformycin, and fludarabine; natural products such as vinca alkaloids (e.g., vinblastine and vincristine); podophyllum derivatives such as etoposide and teniposide; antibiotics such as, bleomycin, dactinomycin, doxorubicin, mithramycin, mitomycin, mitoxantrone; hormones and hormone antagonists; androgens such as halotestin, testolactone; corticosteroids such as prednisone and dexamethasone; estrogens such as dethylstilbestrol; progestins megestrol acetate and medroxyprogesterone acetate; estrogen antagonists tamoxifen and taxol; androgen antagonists such as flutamide; LHRH agonists such as leuprolide and goserelin; substituted ureas such as hydroxyurea; methylhydrazine derivatives such as procarbazine; adrenocortical suppressants such as mitotane; steroid synthesis inhibitors such as aminoglutethemide; and substituted melamines such as altretamine. Examples of biological response modifiers include, but are not limited to, interferons such as interferon alpha and interferon gamma; interleukins such as IL-2; and tumor necrosis factor. Examples of radiopharmaceuticals include, but are not limited to, meta-iodobenzylguanidine (MIBG) and 111In-labeled somatostatin analog [diethylenetriaminepentaacetic acid (DTPA)-DPhe1]-octreotide. Examples of cell toxins includes tirapazamine and others. Examples of radiation sensitizers include, but are not limited to, nitroimidazoles such as misonidazole, etanidazole, metronidazole, and nimorazole;

docetaxel, paclitaxel, idoxuridine, fludarabine, gemcitabine, and taxanes. Examples of genetic materials include, but are not limited to, chromosome(s), DNA, cDNA, genomic DNA, mRNA, polynucleotide(s), oligonucleotide(s), nucleic acid(s), any synthetic DNA and RNA sequences, and sense and antisense nucleic acid(s). The liposomes of the instant invention can deliver therapeutic agents to specific sites in the body. For example, the liposomes can selectively localize anti-cancer drugs or other agents at a tumor site, resulting in markedly reduced toxicity in addition to improved therapeutic activity due to higher drug levels being delivered to the tumor.

The use of ionizing radiation in the treatment of cancer has spawned it's own medical specialty, radiation oncology. Furthermore, the use of ionizing radiation is a key component of the cancer treatment triad such as surgery, radiation, and chemotherapy. Clinically, the use of ionizing radiation is widespread, and its methods are tremendously sophisticated. Highly defined regions can be irradiated with increasingly homogenous doses. In cancer therapy, radiation and surgery are used primarily in establishing local control of a disease, while chemotherapy is able to reach disseminated disease. However, improved local control alone would have significant effects on clinical outcomes. A significant number of invasive cancers are locally confined at initial diagnosis. Hence, the failure to control a primary tumor results in both increased rates of metastasis and increased numbers of metastatic sites. Thus, improvements in radiation and surgery to provide more effective local control would have a significant impact on clinical outcomes for patients with any of a wide variety of solid tumors. Sterically stabilized liposomes can stay in circulation for extended periods of time and accumulate at tumor sites. Therefore the coupling of localized radiation to trigger the release of agents at these sites provides a significant advantage in local tumor control. Consequently, the use of radiation sensitive liposomes holds tremendous promise in the treatment of disease.

e) Radiation Sensitive Liposomes as Diagnostics

In another embodiment, the instant invention provides for a method of diagnosing the presence or progression of a disease, comprising the steps of (i) administering to a patient a pharmaceutical composition comprising a liposomal delivery system and releasable agent such as a diagnostic agent, wherein the releasable agent is encapsulated in or associated with the liposome, and a pharmaceutically acceptable carrier or diluent; (ii) subjecting the patient to ionizing radiation in order to destabilize the liposome and release the diagnostic agent encapsulated in or associated with the liposome; and (iii) diagnosing the disease through use of molecular imaging techniques. In one embodiment, the radiation dosage ranges from about 5 to about 500 rads. In a preferred embodiment, the radiation dosage ranges from about 50 to about 250 rads. Examples of diagnostic agents include, but are not limited to, contrast agents, iodinated agents, radiopharmaceuticals, antibodies, fluorescent compounds and fluorescent compounds coencapsulated with a quencher, agents containing MRS/MRI sensitive nuclides, and genetic material encoding contrast agents. Examples of contrast agents include, but are not limited to, gadolinium-diethylenetriaminepentaacetic acid (GdDTPA; Magnavist), aka gadopentetate dimeglumine, gadoteridol (ProHance), gadodiamide, gadoterate meglumine, gadobenate dimeglumine (Gd-BOPTA/Dimeg; Multi-Hance), mangafodipir trisodium (Mn-DPDP), ferumoxides, paramagnetic analogue of doxorubicin, and ruboxyl (Rb). Examples of iodinated agents include, but are not limited to, diatrizoate (3,5-di(acetamido)-2,4,6-triiodobenzoic acid), iodipamide (3,3'-adipoyl-diimino-di(2,4,6-triiodobenzoic acid), acetrizoate[3-acetylamino-2,4,6-triiodobenzoic acid], aminotrizoate[3-amino-2,4,6-triiodobenzoic acid]), and iomeprol. Examples of radiopharmaceuticals include, but are not limited to, fluorine-18 fluorodeoxyglucose ([18F]FDG), Tc-99m Depreotide, carbon-11 hydroxyephedrine (HED), [18F]setoperone, [methyl-11C]thymidine, 99 mTc-hexamethyl propyleneamine oxime (HMPAO), 99 mTc-L, L-ethyl-cysteinate dimer (ECD), 99 mTc-sestamibi, thallium 201, I-131metaiodobenzylguanidine (MIBG), 123I-N-isopropyl-p-iodoamphetamine (IMP), 99 mTc-hexakis-2-methoxy-isobutylisonitrile (MIBI), 99 mTc-tetrofosmin. Examples of agents containing MRS/MRI sensitive nuclides include, but are not limited to, perfluorocarbons and fluorodeoxyglucose. Examples of genetic material encoding contrast agents include, but are not limited to, paramagnetic reporter genes such as ferredoxin; paramagnetic tag(s) on liposomal lipids such as paramagnetic chelating groups added to PEG; detectable probes; and luciferin/luciferase reporter system. Examples of molecular imaging techniques include, but are not limited to, Nuclear Magnetic Resonance (NMR), Magnetic Resonance Spectroscopy/Magnetic Resonance Imaging (MRS/MRI), X-ray/computed axial tomography (CT), Positron Emission Tomography (PET), Single-photon Emission Computed Tomography (SPECT), ultrasound, and optical based imaging techniques. Examples of conditions that can be diagnosed via liposome-encapsulated or associated diagnostic agents include, but are not limited to, cancer, immune disorders, developmental disorders, and genetic disorders. The liposomes of the present invention can deliver diagnostic agents to specific sites in the body. For example, the liposomes can selectively localize diagnostic agents at tumor sites, thereby allowing for detection and diagnosis of various malignancies. Liposomes may be targeted to such tumor sites through the attachment of antibodies, antibody fragments, antigens, peptide sequences, peptide fragments, and the like (supra). For example, liposomes with a specific epitope attached may be targeted to a tumor tissue. After binding of the epitope to the receptor of the tumor tissue, the liposomes are irradiated to release their diagnostic contents. Molecular imaging techniques can then be employed to scan and record the diagnostic agents released by the liposomes. This allows for early detection of tumors and other malignancies. Alternatively, radiation sensitive liposomes can be tagged with dyes, fluorescent molecules, radioisotopes, or the like, for purposes of monitoring their progressive travel to tumor sites. Once the liposomes have arrived at a tumor site, the liposomes are irradiated to release their diagnostic contents which can than be used to measure the grade of invasion of the tumor.

f) Examples

The following specific examples are intended to illustrate the invention and should not be construed as limiting the scope of the claims. The examples further illustrate some of the specifics of destabilization of liposomes and methods employed.

I. Radiation Sensitive Liposomes
1.1 Methods
1.1.1 Materials

The polymerizable lipids were synthesized via procedures we have published (Lamparski et al., *Biochemistry* 1992, 31:685-694; Sells et al., *Macromolecules* 1994, 27:226-233; Lamparski et al., *Macromolecules* 1995, 28:1786-1794). Lipid structure was determined by H-NMR, $^{13}$C-NMR, and mass spectrometry. The purity was examined by thin-layer chromatography with chloroform/methanol/water (65:25:4 by volume) and differential scanning calorimetry (Lamparski et al., *J. Am. Chem. Soc.* 1993, 115:8096-8102). Pure lipids eluted to a single spot with an $R_f$ of 0.35-0.40, and exhibited a sharp highly cooperative main phase transition temperature. Stock benzene solutions of polymerizable lipids (ca. 20 mg/ml) were stored at −40° C. as an amorphous ice. 1,2-Dioleoyl-sn-glycero-3-phosphatidylcholine (DOPC) and distearoyl-sn-glycero-3-phosphatidylcholine (DSPC) were purchased (Avanti Polar Lipids, Inc.) as 20 mg/ml solution in $CHCl_3$ and stored at −40° C. Buffers and EDTA were purchased (Sigma-Aldrich, Inc.) for buffer preparations and used as received. All buffer solutions were prepared with Milli-Q water (Millipore, Inc.). 8-Aminonaphthalene-1,3,6-trisulfonic acid disodium salt (ANTS) and p-xylenebispyridinium bromide (DPX) were purchased (Molecular Probes, Inc.) as solids and stored at −20° C.

1.1.2 Preparation of Liposomes

The lipids used to prepare the liposomes were each dried under an argon stream followed by drying under vacuum (i.e., vacuum dessication) for more than two hours and then weighed. This procedure removed the solvent and provided a dry, thin lipid film. Hydration of the lipid film occurred upon addition of aqueous buffer followed by vortex mixing at temperatures greater than the main phase transition temperature to loosen the film from the flask walls. The lipids were hydrated in the desired molar ratio, including the agents to be encapsulated. The hydrated bilayers were converted into liposomes through the following procedure: Ten freeze/thaw cycles consisting of freezing by submersion of the solution vial into −78° C. dry ice/isopropanol bath followed by thawing in a 37° C. bath, insuring the lipids were well hydrated and were in extended bilayers. The lipid bilayers were converted to liposomes of defined size by extrusion at 37° C. through 2 stacked 100 nm pore size Nuclepore brand polycarbonate filters through a stainless extrusion apparatus (Lipex Biomembranes, Inc.). The liposomes were purified by elution through a gel permeation chromatography column with an isoosmotic buffer to remove unencapsulated agents. The liposome size distributions were measured by dynamic light scattering. Multiangle dynamic laser light scattering provided vesicle diameter distributions upon analysis of data obtained from 90°−, 60°− and 120° angle using various fitting methods, i.e., single exponential sampling, non-negatively constrained least squares and CONTIN as previously published (Koelchens et al., *Chem. Phys. Lipids* 1993, 65:1-10). Liposomes were 100±10 nm in diameter.

1.2 Results

The relative sensitivity to ionizing radiation of liposomes composed of either bis-SorbPC (1; FIG. 5), bis-DenPC (2; FIG. 5), or bis-AcrylPC (3; FIG. 5) was investigated. These polymerizable colipids have different reactivities that control the initial rate of polymerization, extent of polymerization, and inhibition by oxygen. The interaction of ionizing radiation with water produces radical species that can initiate radical chain polymerizations. Radical polymerization of acryloyl monomers generally occurs at a faster rate than diene containing monomers, such as the dienoyl and sorbyl esters, because the propagating radicals are less stable (Odian, G., *Principles of Polymerization*, 1991, John Wiley & Sons, New York).

The rate of the ionizing radiation initiated polymerization (Rp) of liposomes composed of either bis-SorbPC, bis-DenPC, or bis-AcrylPC was determined by the loss of monomer absorption intensity. The maximum dose rate at the liposome samples was $2.1 \times 10^4$ rad/h. This intensity could be attenuated if desired. The ionizing radiation initiated polymerization of bis-SorbPC and bis-DenPC was relatively insensitive to the presence of dissolved oxygen in the aqueous buffer, whereas the polymerization of bis-AcrylPC was inhibited by oxygen. There was no change in the monomer concentration even after 120 minutes of irradiation at the maximum dose rate. Radical polymerization of acryloyl functionalities are very sensitive to oxygen due to the high energy of the propagating species. In contrast, if the bis-AcrylPC liposome suspension was purged of oxygen the monomer could be converted to polymer in a few minutes. The Rp for bis-SorbPC liposomes in water (with or without oxygen present) was about twice that of bis-DenPC liposomes. The liposomes composed of bis-AcrylPC (without oxygen) were about 10 times more reactive than bis-SorbPC liposomes. These results are similar to those obtained for the polymerization of these monomers via the generation of radicals from thermal initiators.

We showed that the extent of polymerization of bis-SorbPC and bis-AcrylPC was independent of whether the exposure to ionizing radiation was continuous or discontinuous. The usual experimental protocol for radiation exposure of the liposome samples utilized discontinuous exposure because samples for all the time points were exposed together. Hence, the source was on to expose the samples and switched off to permit sample retrieval at each time point. In some experiments the samples were exposed continuously. The percent loss of monomer depended on the total exposure, but was insensitive to whether the radiation was delivered in a continuous or punctuated manner.

II. Ionizing Radiation as a Trigger for PEG-Liposome Destabilization

In order to determine whether relatively low doses of ionizing radiation, i.e., comparable to therapeutic doses, could be effective in destabilizing. PEG-liposomes, liposomes were prepared with encapsulated water soluble fluorescent markers. The release of these markers was then determined as a function of the dose of ionizing radiation. The following experiments demonstrate that doses as low as 50 rads can cause the release of water soluble markers from PEG-liposomes.

2.1 Methods 2.1.1 Liposome Preparation

The polymerizable lipids used, and the preparation of the liposomes are all as described in Section 1 (supra).

2.1.2 Liposomal Irradiation

After preparation and purification via column chromatography, liposomes coencapsulating ANTS and its collisional quencher DPX were irradiated using a Cobalt-60 teletherapy unit (Arizona Cancer Center Experimental Radiation Facility). Irradiation was carried out at doses ranging from 0 to 1000 rads. Leakage, was assessed at time points ranging from 0 to 36 hours.

2.1.3 Liposome Destabilization

The radiation induced release of liposomal contents was monitored by dequenching of ANTS fluorescence as ANTS and DPX (collisional quencher of ANTS fluorescence) were released and diluted into the bulk aqueous phase (Bennett et al., *Biochemistry* 1995, 34:3102-3113; Ellens et al., *Biochemistry* 1985, 24:3099-3106). The liposome population coencapsulated ANTS and DPX by preparing them in equal amounts in the two buffers:

Buffer 1: 25 mM ANTS, 63 mM NaCl, 10 mM glycine, pH 9.5, 230 mOs

Buffer 2: 90 mM DPX, 10 mM glycine, pH 9.5, 230 mOs

Untrapped ANTS/DPX were separated from the liposomes by passing the suspension over a SEC column packed with high resolution Sephacryl S-300 gel. Leakage was monitored by fluorescence dequenching vs. time with excitation at 360 nm and emission observed at 520 nm. The sample cell holder was thermostatted to the appropriate temperature and the sample was continuously stirred. The 100% leakage value was obtained by lysing the liposomes with excess Triton X-100. Time based fluorescence scans were converted to % leakage vs. time (seconds) plots using the following equation:

$$100 \times I_t - bI_o / I_{triton} - bI_o$$

where $I_t$ refers to the fluorescence intensity at some time t, $I_o$ is the initial fluorescence value and $I_{triton}$ is the relative fluorescence after 100% leakage due to triton lysis of vesicles corrected for change in concentration, and b is a bleaching factor to correct for any bleaching due to ionizing irradiation of the fluorescent dye, ANTS, during the experiment.

2.2 Results

In order to assess the effect of ionizing radiation on polymerizable PEG-liposomes, various liposome compositions were prepared. The lipid ratios used for preparation of the PEG-liposomes compositions were the following:

Composition 1: $PEG_{2000}$-dioleoylPE, cholesterol, dioleoylPC, and bis-$SorbPC_{17,17}$ (molar ratio: 15/40/20/30)

Composition 2: $PEG_{2000}$-distearoylPE, cholesterol, distearoylPC, and bis-$SorbPC_{17,17}$ (molar ratio: 15/40/20/30)

For liposomes prepared from Composition 1, significant release was observed at doses as low as 250 rads. Increasing release was observed for a given dose with increasing time. Increasing release was also observed with increasing doses up through 2500 rads. For liposomes prepared from Composition 2, significant release was observed at doses as low as 50 rads. Increasing release was seen with increasing doses up to 200-250 rads. Radiation doses higher than 250 rads show little or no significant increases in release. At all doses examined, no significant increases in release were observed over time.

Additional PEG-liposome compositions used to test the release of liposomal contents were the following:

Composition 3: $PEG_{2000}$-distearoylPE, distearoylPC, and bis-$SorbPC_{17,17}$ (molar ratio 5/75/20)

Composition 4: $PEG_{2000}$-dioleoylPE, cholesterol, dioleoylPC, and bis-$SorbPC_{17,17}$ (molar ratio 15/35/18/31)

Composition 5: $PEG_{2000}$-distearoylPE, cholesterol, distearoylPC, and bis-$SorbPC_{17,17}$ (molar ratio 16/35/20/28)

Composition 6: $PEG_{2000}$-distearoylPE, cholesterol, distearoylPC, and bis-$SorbPC_{17,17}$ (molar ratio 15/35/20/30)

Composition 7: $PEG_{2000}$-distearoylPE, cholesterol, distearoylPC, and bis-$SorbPC_{17,17}$ (molar ratio 15/34/21/30)

Given that clinical doses in current cancer therapy are typically 2 Gy (200 rads), these experiments clearly demonstrate the potential clinical utility of radiation-induced liposomal destabilization for the treatment of cancer. They also suggest that adjustment of the exact lipid composition of the liposome may permit tailoring the release to meet specific needs, i.e., significant release with minimal irradiation or increasing release over time after irradiation. These data further suggest that significant release can be achieved at sub-clinical doses, suggesting the potential use of ionizing radiation as a trigger for liposomal release for the treatment of other non-cancerous conditions.

III. Ionizing Radiation Induced Release of Doxorubicin

In order to further investigate the release of encapsulated agents from the radiation sensitive liposomes, we conducted additional experiments that measured doxorubicin release. Our experiments indicated that 100-200 rads were required to cause significant leakage of encapsulated doxorubicin from the PEG-liposomes. Thus, as the following experiments demonstrate, we have shown that doses even as low as 100 to 200 rads can cause the release of encapsulated agents from PEG-liposomes.

3.1 Methods 3.1.1 Liposome Preparation

The lipid ratios used for preparation of the PEG-liposomes composition used in this experiment were the following:

Composition 8: $PEG_{2000}$-distearoylPE, cholesterol, distearoylPC, and bis-$SorbPC_{17,17}$ (molar ratio 4/34/42/20).

The liposomes were hydrated with 3 mL of 1.20 mM $(NH_4)_2SO_4$ (in MilliQ water, pH 7.0). The sample was freeze/thawed ten times at dry ice/isopropanol and 60° C. The sample was then extruded twice through a series of decreasing size Nuclepore filters with the smallest pores being 100 nm diameter. The liposomes were stored in a refrigerator overnight. The next day the ammonium sulfate was removed from the outside of the liposomes by exchange with aqueous NaCl (pH 7.0, 270 mOsm=isoosmotic) on a Sephadex G-75 column. The total lipid concentration of the fraction from the column was 2.77 mM.

Doxorubicin (0.5 mM, 10 mg/ml in MilliQ water) was added and incubated with the liposome sample for 15 minutes at 30° C. The sample was kept on ice for a few minutes and was then equilibrated for 5 minutes, before the next column was run. This Sephadex G-75 column exchanged the doxorubicin from the outside of the PEG-liposomes with aqueous NaCl (pH 7.0, 270 mOsm=isoosmotic). The collected liposomes were used to determine their sensitivity to ionizing radiation.

3.2. Results

The radiation induced release of doxorubicin was determined (in triplicate) by, the increased fluorescence of each sample. An exposure of 100 rads resulted in the release of 50% of the doxorubicin. When the exposure was 200 rads, 90% of the doxorubicin was released, thus demonstrating that doses as low as 100 to 200 rads can cause the release of encapsulated therapeutic agents from radiation sensitive liposomes.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims.

What is claimed is:

1. A method of enhancing ionizing radiation therapy in the treatment of cancer in a human patient comprising:
   administering to the patient an ionizing radiation sensitive liposome that is unpolymerized at room temperature, the liposome comprising a stable liposome forming lipid and a polymerizable colipid produced by the method of:
   (i) selecting a stable liposome-forming lipid or lipids, and an ionizing radiation polymerizable colipid or colipids, wherein said polymerizable colipid comprises a polymerizable group selected from the group consisting of diacetylenyl, acryloyl, methacryloyl, dienoyl, dienyl, sorbyl, muconyl, styryl, vinyl, and lipoyl;
   (ii) drying the lipids and colipids that comprise the liposome;
   (iii) hydrating the lipids and colipids with a buffer comprising releasable agents to be encapsulated or associated in a desired molar ratio to form liposomes at a temperature which enables the colipids to cluster in discrete domains in said liposomes; and purifying the liposomes to yield an administrable agent comprising a radiation sensitizer or radiopharmaceutical;

wherein after administration to the patient the colipids in the liposomes remain clustered in discrete domains and at least a fraction of the polymerizable colipid polymerizes upon exposure to the ionizing radiation; and administering the ionizing radiation therapy to target at least one tumor site of the patient; thereby destabilizing the membrane of the liposome; and releasing the administrable agent at the targeted site(s), whereby the ionizing radiation therapy is enhanced.

2. The method of claim 1, wherein the agent is a radiation sensitizer.

3. The method of claim 1, wherein the agent is a radiopharmaceutical.

4. The method of claim 1, wherein the liposome comprises from about 2% to about 40% polymerizable colipid.

5. The method of claim 1, wherein the liposome further comprises a steric stabilizer.

6. The method of claim 5, comprising from about 2% to about 20% of the steric stabilizer.

7. The method of claim 1 wherein the liposome is targeted to the cancer site through attachment of at least one targeting peptide to the liposome.

8. The method of claim 7, wherein the peptide is an antibody or an antibody fragment.

9. The method of claim 7, wherein the ionizing radiation is administered in a dose of 5 to 500 rads.

10. The method of claim 7, wherein the ionizing radiation is administered in a dose of 50 to 250 rads.

* * * * *